(12) United States Patent
Dietz et al.

(10) Patent No.: US 8,487,487 B2
(45) Date of Patent: Jul. 16, 2013

(54) MAGNETOSTRICTIVE ACTUATOR OF A MEDICAL ULTRASOUND TRANSDUCER ASSEMBLY, AND A MEDICAL ULTRASOUND HANDPIECE AND A MEDICAL ULTRASOUND SYSTEM HAVING SUCH ACTUATOR

(75) Inventors: Timothy G. Dietz, Terrace Park, OH (US); Hans Jaeger, Thunstetten (CH)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 875 days.

(21) Appl. No.: 12/501,524

(22) Filed: Jul. 13, 2009

(65) Prior Publication Data

US 2010/0016728 A1     Jan. 21, 2010

Related U.S. Application Data

(60) Provisional application No. 61/080,772, filed on Jul. 15, 2008.

(51) Int. Cl.
*H02N 2/00* (2006.01)

(52) U.S. Cl.
USPC ............................................ 310/26; 600/459

(58) Field of Classification Search
USPC ... 310/26; 600/459; 606/1, 205, 169; 433/36, 433/119, 186, 132
See application file for complete search history.

(56) References Cited

U.S. PATENT DOCUMENTS

| | | | |
|---|---|---|---|
| 3,589,363 A | | 6/1971 | Banko et al. |
| 3,930,173 A | * | 12/1975 | Banko .............................. 310/26 |
| 4,033,791 A | * | 7/1977 | Kaczkowski ................. 148/310 |
| 4,986,808 A | | 1/1991 | Broadwin et al. |
| 5,382,162 A | | 1/1995 | Sharp |
| 5,395,240 A | | 3/1995 | Paschke et al. |
| 5,850,109 A | * | 12/1998 | Mock et al. ..................... 310/26 |
| 5,958,154 A | | 9/1999 | O'Handley et al. |

(Continued)

FOREIGN PATENT DOCUMENTS

| | | |
|---|---|---|
| EP | 1705670 | 9/2006 |
| JP | 2008-069434 | 3/2008 |
| WO | 03/093520 | 11/2003 |

OTHER PUBLICATIONS

PCT, International Preliminary Report on Patentability, International Application No. PCT/US2009/050525 (Jan. 18, 2011).

(Continued)

*Primary Examiner* — Tran Nguyen
*Assistant Examiner* — Leda Pham
(74) *Attorney, Agent, or Firm* — Thompson Hine L.L.P.

(57) ABSTRACT

Apparatus includes a magnetostrictive actuator of a medical ultrasound transducer assembly. The actuator comprises a magnetostrictive alloy chosen from a list. A medical ultrasound handpiece includes an ultrasound transducer assembly adapted to attachingly receive an end effector. The transducer assembly includes a magnetostrictive actuator having a magnetostrictive alloy, and includes a first coil surrounding the actuator and adapted to excite the actuator to substantially a desired medical resonant frequency and substantially a desired medical amplitude. A medical ultrasound system includes a handpiece housing, a first medical ultrasound transducer assembly, and a first medical end effector attachable to the first transducer assembly. The first transducer assembly includes a magnetostrictive first actuator having a first magnetostrictive alloy. At least a portion of the first transducer assembly is attachingly insertable in the handpiece housing without the use of tools, without damaging the handpiece housing, and without damaging the first transducer assembly.

26 Claims, 12 Drawing Sheets

U.S. PATENT DOCUMENTS

| | | | |
|---|---|---|---|
| 5,980,251 A | | 11/1999 | Sullivan et al. |
| 6,164,968 A | * | 12/2000 | Feine .......................... 433/119 |
| 6,550,745 B2 | | 4/2003 | Bergstrom et al. |
| 6,624,539 B1 | | 9/2003 | Hansen et al. |
| 7,083,589 B2 | | 8/2006 | Banko et al. |
| 2004/0195541 A1 | * | 10/2004 | Basheer et al. ............ 252/62.54 |
| 2006/0175912 A1 | * | 8/2006 | Mori et al. ...................... 310/26 |
| 2008/0061264 A1 | | 3/2008 | Maeda et al. |

OTHER PUBLICATIONS

PCT, International Search Report, PCT/US2009/050525, 7 pages (mailed Dec. 28, 2009; published Mar. 11, 2010).

Huston, E.L. et al., "Magnetic and Magnetostrictive Properties of Cube Textured Nickel for Magnetostrictive Transducer Applications," *IEEE Transactions of Magnetics*, vol. MAG-9, (4), pp. 636-640 (Dec. 1973).

Yoo, J-H. et al., "Performance Improvements in Galfenol Laminated Rods with Stress Annealing," Proc. of SPIE, vol. 6929, 69291Y-1 through 69291Y-10 (2008).

Abstract: Summers, E.M. et al., "Magnetic and mechanical properties of polycrystalline Galfenol," *Smart Structures and Materials 2004: Active Materials: Behavior and Mechanics*, edited by Lagoudas, D.C., Proceedings of SPIE, vol. 5387, pp. 448-459 (2004).

McKnight, G.P., "Magnetostrictive Materials Background," http://aml.seas.ucla.edu/research/areas/magnetostrictive/overview.htm (Jun. 2003).

* cited by examiner

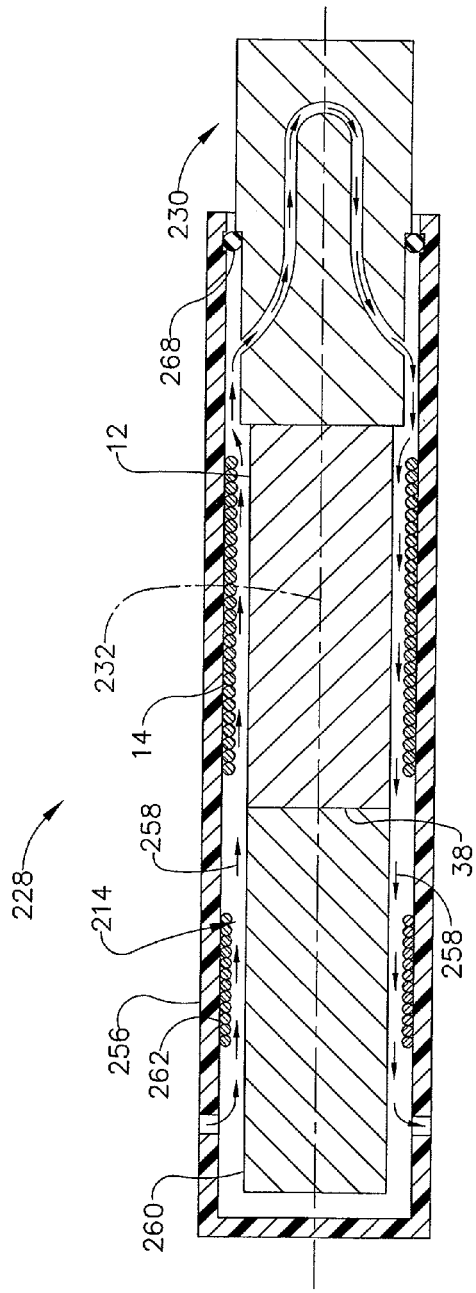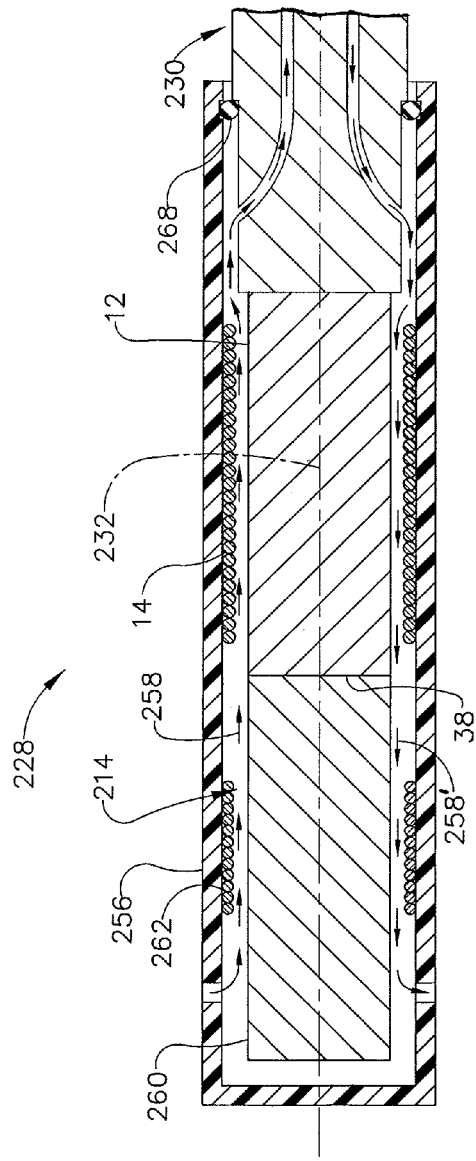
FIG. 6A
FIG. 6B

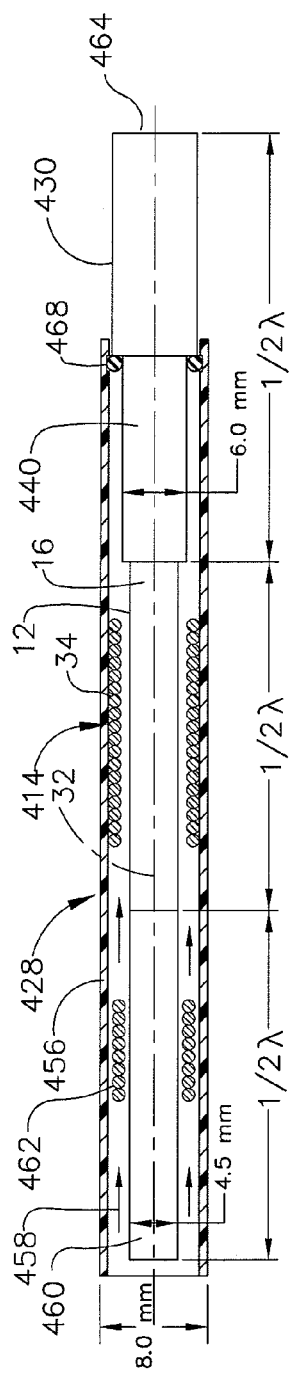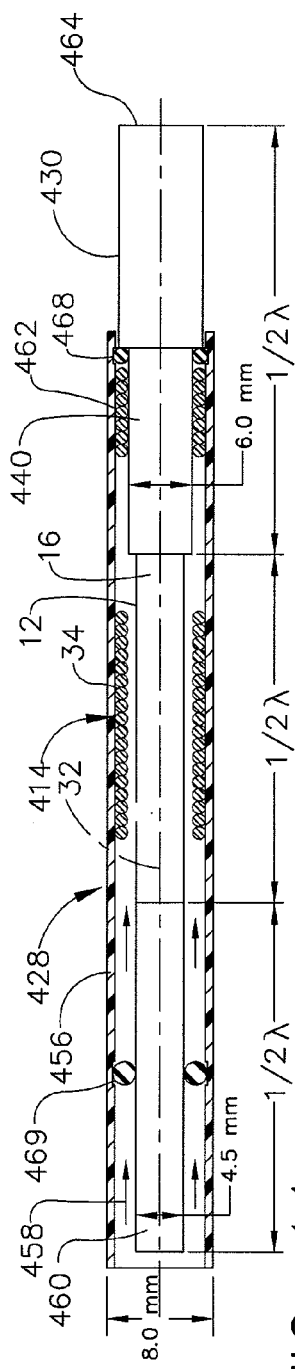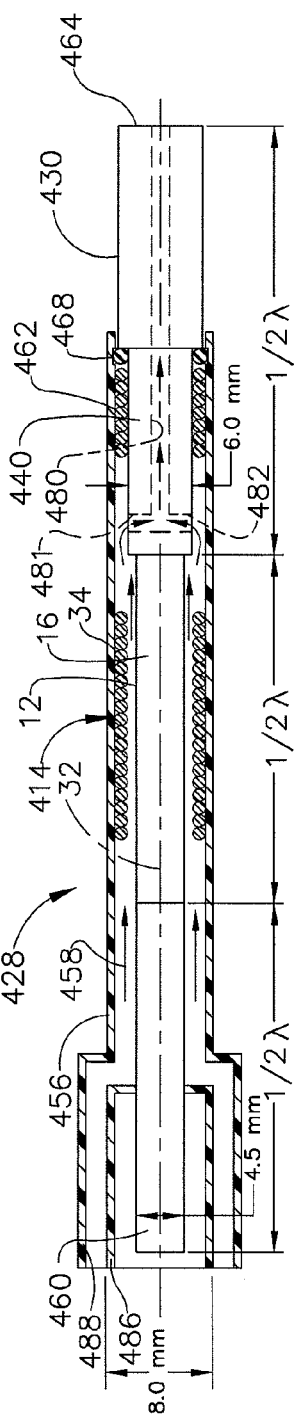

MAGNETOSTRICTIVE ACTUATOR OF A MEDICAL ULTRASOUND TRANSDUCER ASSEMBLY, AND A MEDICAL ULTRASOUND HANDPIECE AND A MEDICAL ULTRASOUND SYSTEM HAVING SUCH ACTUATOR

CROSS REFERENCE TO RELATED APPLICATIONS

The present application claims the priority benefit of U.S. provisional patent application Ser. No. 61/080,772, filed on Jul. 15, 2008.

FIELD OF THE INVENTION

The present invention is related generally to medical equipment, and more particularly to a magnetostrictive actuator of a medical ultrasound transducer assembly, to a medical ultrasound handpiece having such actuator, and to a medical ultrasound system having such actuator.

BACKGROUND OF THE INVENTION

Medical ultrasound systems are known which use a piezoelectric actuator, having a stack of piezoelectric transducer disks, to ultrasonically drive a medical end effector such as a harmonic scalpel. A dental system is known which uses a magnetostrictive actuator made of nickel to ultrasonically drive a dental scaler to clean teeth. A dental system has been developed by ETREMA Products, Inc. of Ames, Iowa which uses a magnetostrictive actuator made of Terfenol-D (an alloy of terbium, dysprosium, and iron metals) to ultrasonically drive a dental scaler. ETREMA is also developing a magnetostrictive material made of GALFENOL (an alloy of gallium and iron) for low frequency use.

Still, scientists and engineers continue to seek improved magnetostrictive actuators of medical ultrasound transducer assemblies, improved medical ultrasound handpieces having such actuators, and improved medical ultrasound systems having such actuators.

SUMMARY

A first expression of a first embodiment of the invention is for apparatus including a magnetostrictive actuator of a medical ultrasound transducer assembly. The actuator comprises a magnetostrictive alloy chosen from the group consisting of an alloy comprising iron and gallium, an alloy comprising iron and aluminum, an alloy comprising iron, gallium and aluminum, an alloy comprising cobalt, manganese and gallium, an alloy comprising nickel, manganese and gallium, an alloy comprising cobalt, manganese and aluminum, an alloy comprising nickel, manganese and aluminum, an alloy comprising cobalt, nickel, manganese and gallium, an alloy comprising cobalt, nickel, manganese and aluminum, an alloy comprising cobalt, manganese, gallium and aluminum, an alloy comprising nickel, manganese, gallium, and aluminum, and an alloy comprising cobalt, nickel, manganese, aluminum and gallium.

A second expression of the first embodiment of the invention is for a medical ultrasound handpiece including a medical ultrasound transducer assembly adapted to attachingly receive an ultrasonically-driven medical end effector. The transducer assembly includes a central longitudinal axis, includes an elongated magnetostrictive actuator substantially coaxially aligned with the longitudinal axis and comprising a magnetostrictive alloy, and includes a first coil substantially coaxially aligned with the longitudinal axis, surrounding the actuator, and adapted to excite the actuator to substantially a desired medical resonant frequency and substantially a desired medical amplitude. The magnetostrictive alloy is chosen from the group previously described in the first expression of the first embodiment of the invention.

An expression of another embodiment of the invention is for a medical ultrasound system comprising a handpiece housing, a first medical ultrasound transducer assembly, and an ultrasonically-driven first medical end effector attachable to the first medical ultrasound transducer assembly. The first medical ultrasound transducer assembly includes a first central longitudinal axis and includes an elongated magnetostrictive first actuator substantially coaxially aligned with the longitudinal axis and comprising a first magnetostrictive alloy. At least a portion of the first medical ultrasound transducer assembly is attachingly insertable in the handpiece housing without the use of tools, without damage to the handpiece housing, and without damage to the first medical ultrasound transducer assembly. The first magnetostrictive alloy is chosen from the group previously described in the first expression of the first embodiment of the invention.

Several benefits and advantages are obtained from one or more of the expressions of embodiments of the invention. In one example, the magnetostrictive actuator consists essentially of a magnetostrictive alloy chosen from the previously-described group and optionally includes dopants. In this example, the magnetostricitve alloy should provide a ductile magnetostrictive actuator (unlike the brittle Terfenol-D alloy of the known dental scaler which would need to be compressed for durability). In this example, the higher-magnetic-saturation limit of the chosen magnetostrictive alloy should be able to be housed in a small-diameter, ergonomic handpiece housing and drive a larger-diameter medical end effector (compared to the smaller-diameter end effector of the known dental scaler having the nickel actuator, such smaller diameter providing a necessary acoustic gain because of the lower magnetic saturation limit of nickel). It is noted that dental scalers are low power devices used to remove scale from teeth and are not powerful enough to efficiently sculpt teeth or remove bone, whereas examples of the embodiments of the invention should be able to sculpt teeth and cut bone.

The apparatus, medical ultrasound handpiece, and the medical ultrasound system having the magnetostrictive alloy discussed herein are applicable to dental procedures, but they are not limited thereto. Instead the apparatus, medical ultrasound handpiece, and the medical ultrasound system are applicable for general cutting, remodeling, and sealing of biological tissues, for example soft, cartilaginous, and bony tissues.

BRIEF DESCRIPTION OF THE FIGURES

FIGS. 6A and 6B are alternate embodiments of the handpiece of FIG. 5, wherein FIG. 6A shows a handpiece having a recirculation coolant path and FIG. 6B shows a handpiece having an irrigation fluid path and a suction fluid path;

FIGS. 8-12 show additional alternate embodiments of the handpiece of FIG. 5;

DETAILED DESCRIPTION

Before explaining the several expressions of embodiments of the present invention in detail, it should be noted that each expression is not limited in its application or use to the details of construction and arrangement of parts and steps illustrated in the accompanying drawings and description. The illustrative expressions of embodiments of the invention may be implemented or incorporated in other expressions, embodiments, variations and modifications, and may be practiced or carried out in various ways. Furthermore, unless otherwise indicated, the terms and expressions employed herein have been chosen for the purpose of describing the illustrative expressions of an embodiment of the present invention for the convenience of the reader and are not for the purpose of limiting the invention.

It is further understood that any one or more of the following-described expressions, embodiments, examples, etc. can be combined with any one or more of the other following-described expressions, embodiments, examples, etc.

Figure 1:
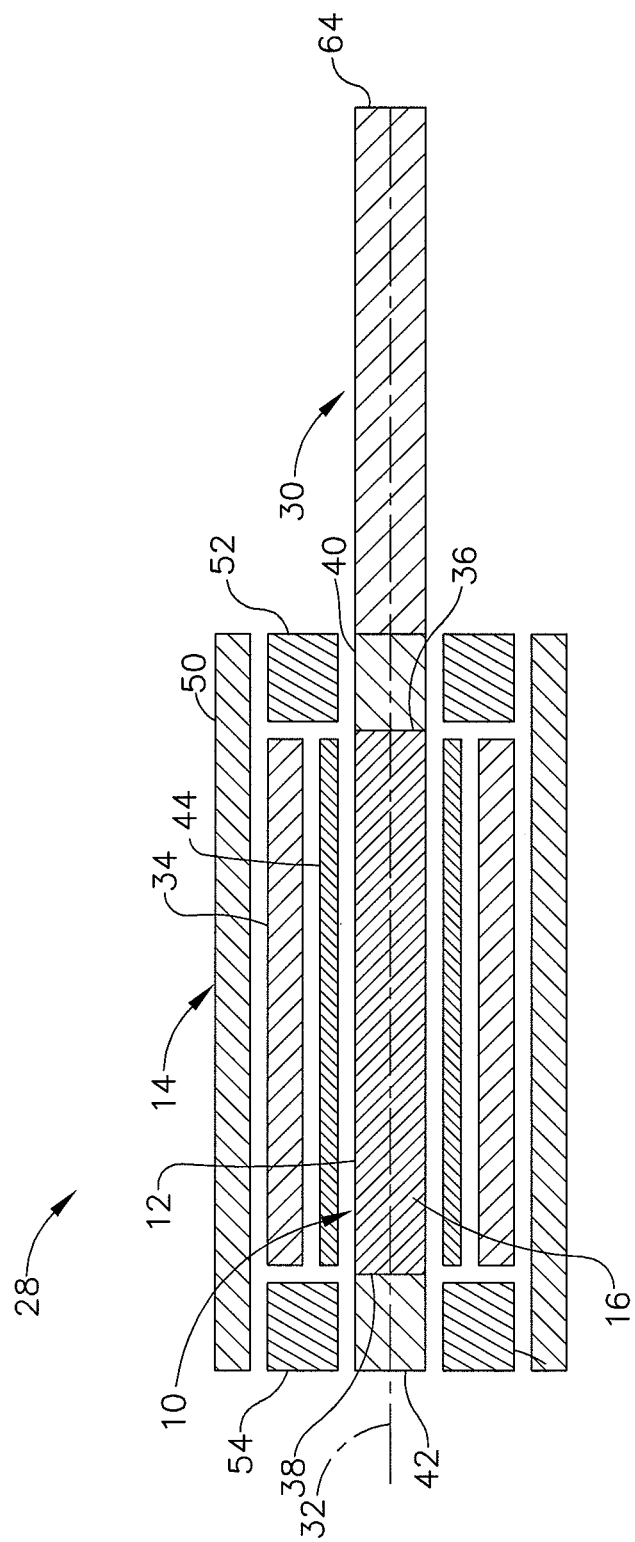
FIG. 1 is a schematic, cross-sectional view of a first embodiment of the invention including a medical ultrasound transducer assembly having a magnetostrictive actuator and also showing an end effector attached to the transducer assembly.

Referring to the drawings, wherein like numerals indicate like elements, a first embodiment of the invention is shown in FIG. 1. A first expression of the embodiment of FIG. 1 is for apparatus 10 including a magnetostrictive actuator 12 of a medical ultrasound transducer assembly 14. The actuator 12 comprises a magnetostrictive alloy 16 chosen from the group consisting of an alloy comprising iron and gallium, an alloy comprising iron and aluminum, an alloy comprising iron, gallium and aluminum, an alloy comprising cobalt, manganese and gallium, an alloy comprising nickel, manganese and gallium, an alloy comprising cobalt, manganese and aluminum, an alloy comprising nickel, manganese and aluminum, an alloy comprising cobalt, nickel, manganese and gallium, an alloy comprising cobalt, nickel, manganese and aluminum, an alloy comprising cobalt, manganese, gallium and aluminum, an alloy comprising nickel, manganese, gallium, and aluminum, and an alloy comprising cobalt, nickel, manganese, aluminum and gallium. In one example, the magnetostrictive actuator 12 consists essentially of a magnetostrictive alloy 16 chosen from the previously described group and optionally includes dopants. Magnetostrictive alloys are commercially available from ETREMA Products, Inc. of Ames, Iowa.

In one enablement of the first expression of the embodiment of FIG. 1, the composition and fabrication process of the magnetostrictive alloy 16 provide a magnetostrictive alloy which substantially meets six properties desired of a magnetostrictive actuator 12 of a medical ultrasound transducer assembly 14. The first property is to be a ductile magnetostrictive alloy (unlike the conventional Terfenol-D magnetostrictive alloy and the piezoelectric transducer disks which are brittle). A ductile magnetostrictive alloy can be used in a non-compressive actuator design and is easier to fabricate into a desired shape. The second property is to have a Curie temperature greater than 250 degrees Fahrenheit to allow for robust thermal operation requiring less, if any, cooling and to allow for routine autoclave sterilization.

The third property is to have a magnetostriction greater than nickel. The magnetostriction of nickel is substantially 30 ppm (parts-per-million). The fourth property is to have a magnetic saturation higher (in one example at least two time higher) than that of nickel. In one embodiment, the fourth property is a magnetic saturation of about 150-300 ppm, and more particularly about 180-245 ppm. The third and fourth properties would allow the handpiece housing surrounding the actuator to have a smaller diameter (such as half the diameter in the one example) compared to a nickel actuator. The fourth property allows the minimization of the amount of acoustic amplification required.

The fifth property is to be able to operate at a medical ultrasound frequency and drive a medical end effector having a cross-sectional area of between and including 1 mm$^2$ and 8 mm$^2$ (and in one example 2.5 mm$^2$) at its distal antinode tip, with a longitudinal, standing-wave vibrational peak-to-peak amplitude at 55.5 kHz between and including 40 microns and 120 microns (and in one example 65 microns). In one illustration, the range of therapeutic output of a 6.4 millimeter-diameter cylindrical titanium medical end effector at 55.5 KHz is 10-30 microns peak-to-peak displacement. In one example, the hysteresis in the transducer actuation curve is minimized, and the stress induced loss in the magnetostrictive coefficient is minimized. Factors affecting such minimization include: alloy composition and dopants; internal stress induced via the fabrication processes such as mechanical rolling, drawings, etc; and annealing conditions including temperature, time, pressure, atmospheric gas, and mechanical, electrical or magnetic bias.

It is noted that "distal" is a portion closer to the patient. It is additionally noted that an "antinode" is a location of maximum magnitude of vibration. Also, examples of tips, without limitation, include tips having a substantially circular or rectangular cross-sectional area. A medical ultrasound frequency is a frequency between and including 20 KHz and 150 KHz (and in one example 55.5 KHz).

The sixth property is to be able to house the medical ultrasound transducer assembly 14 in a handpiece housing having an outer diameter between and including 5 millimeters and 15 millimeters (and in one example 10 millimeters). It is noted that a desired smaller-diameter, more ergonomic handpiece housing together with a desired larger-cross-section end effector having a desired size vibrational amplitude means that minimal or no acoustic gain can be employed.

Figure 2:
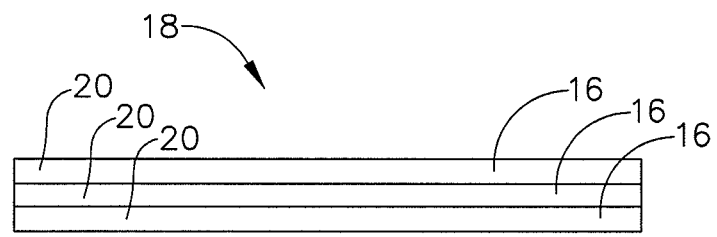
FIG. 2 is a cross-sectional view of a first alternate embodiment of the actuator of FIG. 1 showing a laminated actuator.

In a first fabrication, as shown in the first alternate actuator embodiment of FIG. 2, the magnetostrictive actuator 18 includes a plurality of lamination layers 20 (stacked substantially perpendicular to the main magnetic field) each comprising the magnetostrictive alloy 16. In one variation, the magnetostrictive alloy 16 of each lamination layer 20 is electrically insulated from the magnetostrictive alloy 16 of each neighboring lamination layer 20. Examples of laminations, without limitation, include rolled, machined, and melt-spun ribbon/fiber.

Figure 3:
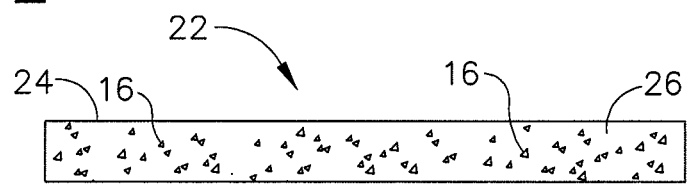
FIG. 3 is a cross-sectional view of a second alternate embodiment of the actuator of FIG. 1 showing a composite actuator.

In a second fabrication, as shown in the second alternate actuator embodiment of FIG. 3, the magnetostrictive actuator 22 comprises a composite material 24, wherein the composite material 24 includes a magnetostrictively-inactive matrix 26 and the magnetostrictive alloy 16, wherein the magnetostrictive alloy 16 is distributed in the matrix 26. In one variation, the magnetostrictive alloy 16 has a first electrical conductivity, and the matrix 26 has a second electrical conductivity which is lower than the first electrical conductivity. Examples of a matrix 26 include a thermoplastic extrusion or molding, a thermosetting epoxy or polyimide, and a kaplon-layer printed film or coating. It is noted that a composite material 24 more easily allows for arbitrary shapes. It is also noted that such laminated magnetostrictive actuators and composite magnetostrictive actuators should reduce undesirable eddy currents and reduce actuator heating.

In a third fabrication, the magnetostrictive alloy 16 is fabricated in bulk such as crystalline, polycrystalline, or amorphus. In one variation, the bulk material of the magnetostrictive actuator 12 is adjusted such that the electrical conductivity of the bulk material is low enough that no lamination (or other technique such as dispersion in a polymer matrix) is required to reduce eddy currents.

A second expression of the embodiment of FIG. 1 is for a medical ultrasound handpiece 28 including a medical ultrasound transducer assembly 14 adapted to attachingly receive an ultrasonically-driven medical end effector 30. The transducer assembly 14 includes a central longitudinal axis 32, includes an elongated magnetostrictive actuator 12 substantially coaxially aligned with the longitudinal axis 32 and comprising a magnetostrictive alloy 16, and includes a first coil 34 substantially coaxially aligned with the longitudinal axis 32, surrounding the actuator 12, and adapted to excite the actuator 12 to substantially a desired medical resonant frequency and substantially a desired medical amplitude. The magnetostrictive alloy 16 is chosen from the group previously described in the first expression of the first embodiment of the invention.

In one application of the second expression of the embodiment of FIG. 1, the desired medical resonant frequency is between and including 20 Khz and 150 Khz (and in one example 55.5 Khz), and the desired medical amplitude is a longitudinal, standing-wave vibrational peak-to-peak amplitude at 55.5 kHz between and including 40 microns and 120 microns (and in one example 65 microns). In one variation, the end effector 30, such as a blade or shears, has a substantially circular or rectangular distal tip having a cross-sectional area of between and including 1 millimeters$^2$ and 8 millimeters$^2$ (and in one example 2.5 millimeters$^2$). In one modification, the end effector 30, when attachingly received by the transducer assembly 14, is driven by the actuator 12 to have a longitudinal, standing-wave vibrational amplitude at its distal antinode tip 64 equal to substantially the vibrational amplitude of the actuator 12.

Figure 4:
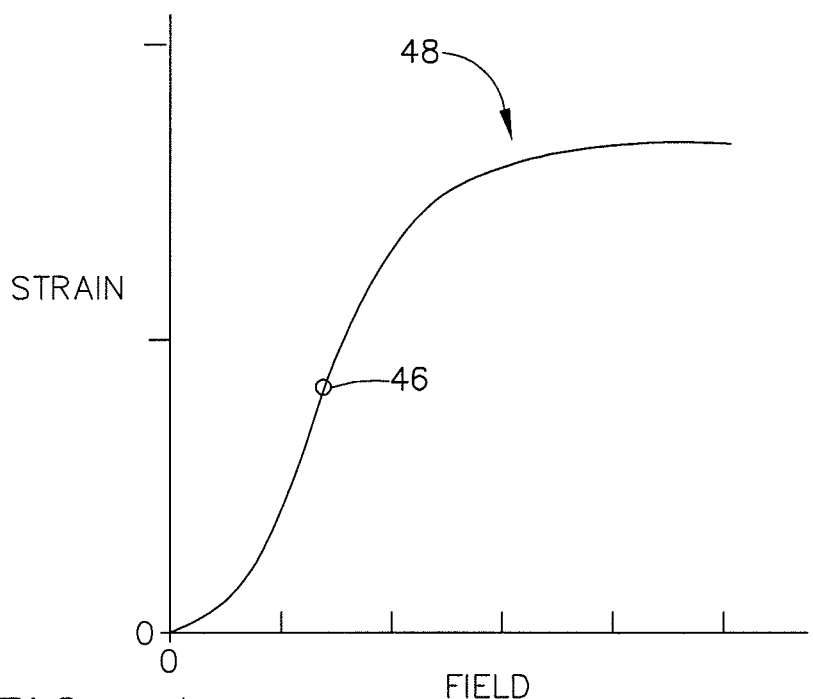
FIG. 4 is a dimensionless example of a strain versus magnetic field graph of the magnetostrictive alloy of the magnetostrictive actuator of FIG. 1 showing a desired operating point on the graph.

In a first enablement of the second expression of the embodiment of FIG. 1, the actuator 12 has first and second ends 36 and 38, wherein the transducer assembly 14 includes a first end mass 40 attached (such as, without limitation, by a threaded stud attachment, by brazing, or by laser welding) to the first end 36 of the actuator 12 and a second end mass 42 attached to the second end 38 of the actuator 12, and wherein the first end mass 40 is adapted to attachingly receive the end effector 30 (such as by a threaded stud arrangement). In one variation, the transducer assembly 14 includes a permanent magnet 44 (or a ferrite magnet, such as, without limitation, a longitudinally slit or laminated ferrite or permanent magnet) substantially coaxially aligned with the longitudinal axis 32, surrounding the actuator 12, and adapted to create a bias magnetic field for a desired operating point 46 on a strain versus magnetic field graph 48 (see FIG. 4) of the magnetostrictive alloy 16. The operating point sets the performance range of the transducer assembly, and in one illustration maximizes the range while minimizing the energy to get to the operating point 46. In one modification, the transducer assembly 14 includes a second coil 50 substantially coaxially aligned with the longitudinal axis 32, surrounding the permanent magnet 44 and the first coil 34, and adapted to adjust the bias magnetic field.

In one example of the first enablement of the second expression of the embodiment of FIG. 1, the transducer assembly 14 includes first and second magnetic field collectors 52 and 54 each substantially coaxially aligned with the longitudinal axis 32 and together longitudinally bounding the first coil 34 and the permanent magnet 44. In one illustration, the first and second end masses 40 and 42 are soft magnetic collectors having low acoustic loss, and the first and second magnetic field collectors 52 and 54 are soft magnetic collectors having low or high acoustic loss. In one construction, the elements of the transducer assembly 14 are held in a plastic molding (not shown)

Figure 5:
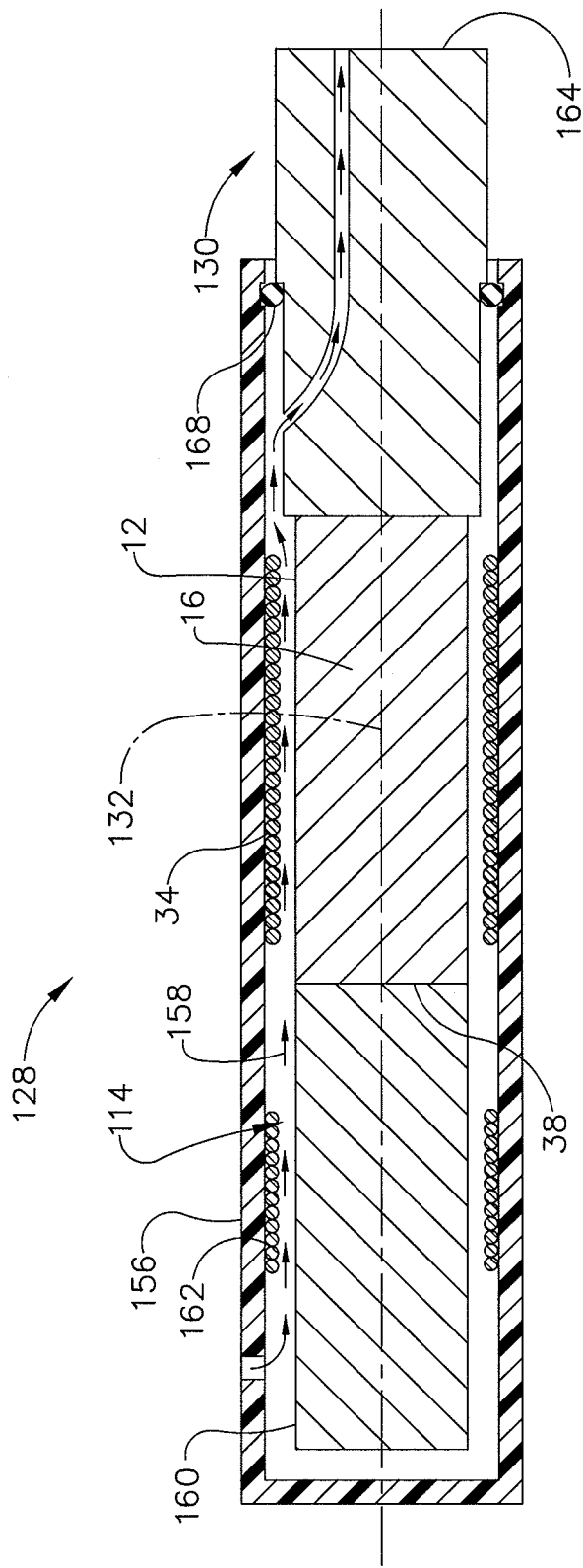
FIG. 5 is a cross-sectional view of a second embodiment of the invention showing a medical ultrasound handpiece including an irrigation/suction fluid path and a sensing coil, wherein some elements of the transducer assembly have been omitted for clarity.

A second embodiment of the invention is shown in FIG. 5. A first expression of the embodiment of FIG. 5 is for a medical ultrasound handpiece 128 including a medical ultrasound transducer assembly 114 adapted to attachingly receive an ultrasonically-driven medical end effector 130. The transducer assembly 114 includes a central longitudinal axis 132, includes an elongated magnetostrictive actuator 12 substantially coaxially aligned with the longitudinal axis 132 and comprising a magnetostrictive alloy 16, and includes a first coil 34 substantially coaxially aligned with the longitudinal axis 132, surrounding the actuator 12, and adapted to excite the actuator 12 to substantially a desired medical resonant frequency and substantially a desired medical amplitude. The magnetostrictive alloy 16 is chosen from the group previously described in the first expression of the first embodiment of the invention. The first coil 34 is transversely spaced apart from the actuator 12. The handpiece 128 includes a handpiece housing 156 and a fluid path 158, wherein the handpiece housing 156 is substantially coaxially aligned with the longitudinal axis 132 and surrounds the first coil 34, and wherein the fluid path 158 includes a portion disposed between the actuator 12 and the first coil 34.

In a first application of the first expression of the embodiment of FIG. 5, the fluid path 158 is at least one of an irrigation and a suction path and is in fluid communication with the end effector 130 when the end effector 130 is attachingly received by the transducer assembly 114. In a second application, as shown in the alternate fluid path embodiment of FIG. 6A, the fluid path 258 of the handpiece 228 between the actuator 12 and the first coil 34 is a recirculation coolant path and is in fluid communication with the end effector 230 when the end effector 230 is attachingly received by the transducer assembly 214. In a third application, as shown in the alternate fluid path embodiment of FIG. 6B, the fluid path 258 of the handpiece 228 is an irrigation fluid path in fluid communication with the end effector 230 and the fluid path 258' of the handpiece 228 is a suction fluid path in fluid communication with the end effector 230 when the end effector 230 is attachingly received by the transducer assembly 214.

In the same or a different application of the first expression of the embodiment of FIG. 5, the transducer assembly 114 includes a resonator end mass 160 and a sensing coil 162. In this application, the actuator 12 has a longitudinal end 38, wherein the resonator end mass 160 is substantially coaxially aligned with the longitudinal axis 132, is acoustically connected to the longitudinal end 38, and has magnetostrictive properties. In this application, the sensing coil 162 is substantially coaxially aligned with the longitudinal axis 132, surrounds the resonator end mass 160, and is adapted to provide feedback on actuator vibrational frequency and actuator vibrational amplitude for controlling the actuator 12 (with the first coil 34) to maintain substantially the desired medical resonant frequency and the desired medical amplitude. It is understood that the desired medical resonant frequency and medical amplitude is substantially maintained to maintain a desired vibrational amplitude of the distal antinode tip 164 of the attached medical end effector 130 even when the attached medical end effector 130 (such as a harmonic scalpel) is under load during, for example, tissue cutting. In a different application, not shown in FIG. 5 or 6, the first coil is disposed proximal the second (sensing) coil for more efficient excitation of the actuator and preferential stimulation of the higher frequency mode.

It is noted that FIG. 6 also shows a handpiece housing 256, a central longitudinal axis 232 of the transducer assembly 214, a resonator end mass 260, a sensing coil 262, and a longitudinal end 38 of the actuator 12. In one example, the resonator end mass 160 and 260 and the end effectors 130 and 230 each comprise aluminum and each are substantially half a wavelength long (as is the actuator 12). The resonator end mass is also called an end bell, and the reduced diameter portion of the end effector is also called a horn.

In the same or a different enablement, as shown in the embodiment of FIG. 5, the actuator 12 is free of mechanical compression.

Figure 7:
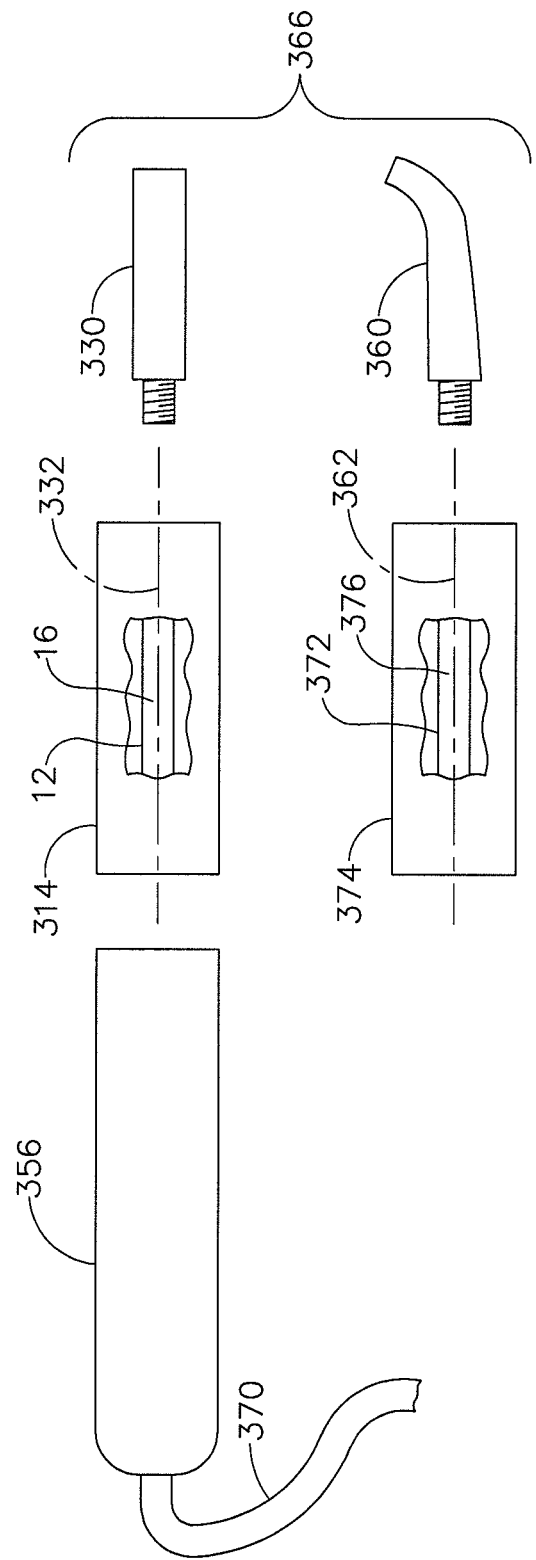
FIG. 7 is a schematic, side elevational view of another embodiment of the invention showing a medical ultrasound system, wherein the medical ultrasound transducer assemblies of the system each have a portion cut-away to expose the magnetostrictive actuator therein.

Another embodiment of the invention is shown in FIG. 7. A first expression of the embodiment of FIG. 7 is for a medical ultrasound system 366 comprising a handpiece housing 356, a first medical ultrasound transducer assembly 314, and an ultrasonically-driven first medical end effector 330 attachable to the first medical-ultrasound transducer assembly 314. The first medical ultrasound transducer assembly 314 includes a first central longitudinal axis 332 and includes an elongated magnetostrictive first actuator 12 substantially coaxially aligned with the longitudinal axis 332 and comprising a first magnetostrictive alloy 16. At least a portion of the first medical ultrasound transducer assembly 314 is attachingly insertable in the handpiece housing 356 without the use of tools, without damage to the handpiece housing 356, and without damage to the first medical ultrasound transducer assembly 314. The first magnetostrictive alloy 16 is chosen from the group previously described in the first expression of the first embodiment of the invention. The first magnetostrictive alloy 16 having the fourth property discussed above, in particular the higher magnetic saturation in a broader range of ppm, enables the operation of a wider range of medical end effectors.

The first medical ultrasound transducer assembly 314 is sterilizable and re-useable. The first medical ultrasound transducer is typically sterilized before insertion into the handpiece housing 356 and can be sterilized after removal from the handpiece housing 356 and/or before subsequent use. The first medical ultrasound transducer assembly 314 is sterilizable with or separate from the first medical end effector 330.

It is noted that a transducer assembly attachingly insertable in a handpiece housing can be directly attached to the handpiece housing (such as, without limitation, by an "O"-ring) and/or can be indirectly attached to the handpiece housing by its attached end effector being attached to the handpiece housing (such as, without limitation, by an "O"-ring 168 and 268 as seen in FIGS. 5 and 6).

In one enablement of the first expression of the embodiment of FIG. 7, the first medical ultrasound transducer assembly 314 is (indirectly) attached to the handpiece housing 356 using a sealing "O"-ring for a pure friction fit (see the "O"-rings 168, 268, and 768-770 in FIGS. 5-6, and 15-16). In the same or a different enablement, not shown, the first medical ultrasound transducer assembly 314 is securely mechanically captured in the handpiece housing 356 such as by using locking rings that are spring released by finger actuated depression, by using a depressible latch, or by using a sliding collate. Other enablements are left to those skilled in the art.

In one implementation of the first expression of the embodiment of FIG. 7, the first medical ultrasound transducer assembly 314 is removable from the handpiece housing 356 without the use of tools, without damage to the handpiece housing 356, without damage to the first medical ultrasound transducer assembly 314, and without damage to the first medical end effector 330. The first medical end effector 330 is easily and quickly changeable by the user even during a medical procedure by simply removing the first medical end effector 330 from the ultrasound transducer assembly 314 and replacing it with an alternate medical end effector. In one embodiment, the first medical end effector 330 is a disposable, single use end effector. A kit having a variety of medical end effectors 330 accompanying the medical ultrasound system 366 allows the user to rapidly change end effectors on the same handpiece. Time is very important during many medical procedures, especially for some specialties such as orthopedic surgery and plastic surgery.

In one extension of the first expression of the embodiment of FIG. 7, the medical ultrasound system 366 includes a second medical ultrasound transducer assembly 374 and an ultrasonically-driven second medical end effector 430 attachable to the second medical ultrasound transducer assembly 374. The second medical ultrasound transducer assembly 374 includes a second central longitudinal axis 362 and includes an elongated magnetostrictive second actuator 372 substantially coaxially aligned with the second longitudinal axis 362 and comprising a second magnetostrictive alloy 376. At least a portion of the second medical ultrasound transducer assembly 374 is attachingly insertable in the handpiece housing 356 and is manually removable from the handpiece housing 356 without the use of tools, without damage to the handpiece housing 356, without damage to the second medical ultrasound transducer assembly 374, and without damage to the second medical end effector 360. The second medical end effector 360 is different from the first medical end effector 330. The second magnetostrictive alloy 376 is chosen from the group previously described in the first expression of the first embodiment of the invention.

In one application of the first expression of the embodiment of FIG. 7, the second end effector 360 is attachable to and removable from the second transducer assembly 374 without damage to the second medical end effector 360 and without damage to the second medical ultrasound transducer assembly 374, and the first medical end effector 330 is attachable to and removable from the first medical ultrasound transducer assembly 314 without damage to the first medical end effector 330 and without damage to the first medical ultrasound transducer assembly 314. In the same or a different application, the first medical ultrasound transducer assembly 314 and the first medical end effector 330 together have substantially no acoustic gain, and the second medical ultrasound transducer assembly 374 and the second medical end effector 360 together have substantially no acoustic gain.

In one method associated with the first expression of the embodiment of FIG. 7, before a medical procedure begins, the first medical end effector 330 is attached to the first medical ultrasound transducer assembly 314 and the second medical end effector 360 is attached to the second medical ultrasound transducer assembly 374 using a torquing tool and taking some time, and the first medical ultrasound transducer assembly 314 (with the attached first medical end effector 330) is quickly inserted in and attached to the handpiece housing 356. Then, a first portion of the medical procedure is performed on a patient using the first medical end effector 330. Then, the first medical ultrasound transducer assembly 314 (with the attached first medical end effector 330) is quickly removed from the handpiece housing 356, and the second medical ultrasound transducer assembly 374 (with the attached second medical end effector 360) is quickly inserted in and attached to the handpiece housing 356. Then, a second portion of the medical procedure is performed on the patient using the second medical end effector 360. This shortens the actual time for the medical procedure compared to conventionally removing the first medical end effector from a common piezoelectric medical ultrasound transducer assembly and attaching a second medical end effector to the common piezoelectric medical ultrasound transducer assembly.

In one example of the first expression of the embodiment of FIG. 7, the second medical ultrasound transducer assembly 374 is substantially identical to the first medical ultrasound transducer assembly 314. In another example, they are substantially different. In one variation, each medical ultrasound transducer assembly as a unique identifier for handpiece recognition, and the transducer assembly/end effector combinations are previewed by a generator (not shown), prior to the medical procedure for any initialization setting needed by the generator to efficiently run the combination. The generator is attachable to the transducer assembly by a cable 370 extending from the handpiece housing 356.

The following paragraphs describe other examples of embodiments of the invention.

Figure 8:
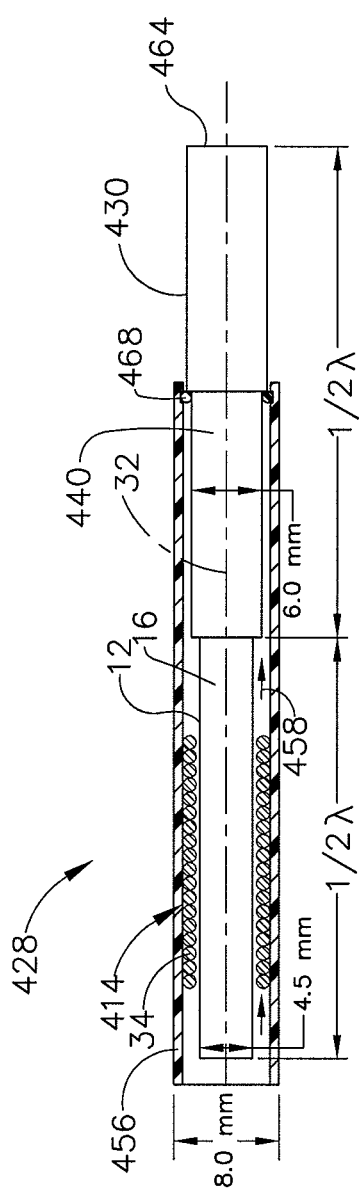

FIGS. 8-12 are views of additional embodiment of the handpiece of FIG. 5 including dimensions, attachment of acoustic components, and/or placement of a sensing coil. In one example of an alternative expression of the embodiment of FIG. 5, as shown in FIG. 8, a medical ultrasound handpiece 428 includes a medical ultrasound transducer assembly 414 having a central longitudinal axis 32, includes an elongated magnetostrictive actuator 12 substantially coaxially aligned with the longitudinal axis 32 and comprising a magnetostrictive alloy 16, and includes a first coil 34 substantially coaxially aligned with the longitudinal axis 32, surrounding the actuator 12, and adapted to excite the actuator 12 to substantially a desired medical resonant frequency and substantially a desired medical amplitude. The magnetostrictive alloy 16 is chosen from the group previously described in the first expression of the first embodiment of the invention. The first coil 34 is transversely spaced apart from the actuator 12 to provide a fluid path 458.

The handpiece 428 includes a handpiece housing 456 substantially coaxially aligned with the longitudinal axis 32 and surrounding the medical ultrasound transducer assembly 414. The handpiece housing 456 partially defines the fluid path 458. A portion of the fluid path 458 is disposed between the actuator 12 and the first coil 434 and is in fluid communication with openings in the end effector 430. The end effector is attachingly received by the transducer assembly and is sealingly connected to the handpiece housing, for example with O-ring 468. The end effector 430 includes a tip 464.

The diameter of the magnetostrictive actuator 12 has a diameter that is smaller than the diameter of the first end mass 440 that attaches the end effector to the magnetostrictive actuator 12. In one embodiment the diameter of the actuator 12 is smaller than the first end mass 440 by about ¼ the diameter of the first end mass. As shown in FIGS. 8-12, the first end mass 440 has a diameter of 6.0 mm and the actuator 12 has a diameter of 4.5 mm and the handpiece has an overall diameter of 8.0 mm.

The magnetostrictive actuator 12 is the length of one-half wavelength. This length provides attachment of the end effector proximate to a vibrational antinode. The length of the end effector 430 including the first end mass 440 is one-half wavelength. To avoid interference with the harmonics of the actuator the O-ring 468 is placed at or proximal a node of the wave.

Figure 9:
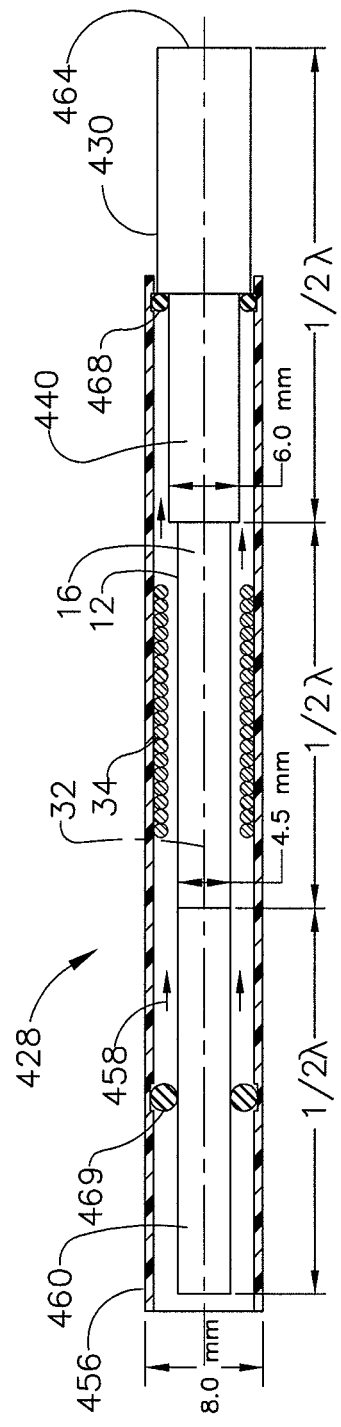

FIG. 9 is the embodiment of FIG. 8 with the addition of a resonator end mass 460 connected to the magnetostrictive actuator 12 at the end opposite the end effector 430. The one-half wavelength of the actuator provides attachment of the resonator end mass 460 or other acoustic components at a vibrational antinode. The second end mass 460 is about one-half wavelength in length and may be about the same diameter as the actuator 12. To seal the handpiece a second O-ring 469 may be disposed between the resonator end mass 460 and the handpiece housing 456 at or proximate a node to avoid interference with the vibrations of the actuator.

FIG. 10 is the embodiment of FIG. 8 with the addition of a resonator end mass 460 and a sensing coil 462. The resonator end mass 460 has magnetostrictive properties, is substantially coaxially aligned with the longitudinal axis 32, and is acoustically connected to the actuator 12 at the end opposite the end effector 430. The sensing coil 462 is substantially coaxially aligned with the longitudinal axis 32 and surrounds the resonator end mass 460. The sensing coil 462 may be disposed at or proximate a node and may be transversely spaced apart from the resonator end mass 460 to provide part of the fluid path 458.

FIG. 11 is the embodiment of FIG. 8 with the addition of a resonator end mass 460, a second O-ring 469, and a sensing coil 462. In this embodiment, the resonator end mass 460 and the O-ring 469 are disposed as explained above for FIG. 9. The sensing coil 462, however, is substantially coaxially aligned with the longitudinal axis 32 and surrounds the first end mass 440 of the end effector 430 proximate the end of the handpiece housing 456 receiving the end effector. In this embodiment the first end mass 440 has magnetostrictive properties.

In a first application of the embodiment of FIG. 11 O-ring 468 and/or O-ring 469 cooperate with the first end mass 440 and the resonator end mass 460, respectively, and may be positioned or applied to pre-stress the magnetostrictive actuator 12 to adjust the operating point and efficiency thereof. In an alternate embodiment of FIG. 11, a stress element may be positioned near O-ring 469 to apply pressure to the resonator end mass 460 to adjust the operating point and efficiency of the magnetostrictive actuator 12. The stress element may be adjustable to change the operating point and efficiency. The stress element may be an adjustable bolt in contact with the resonator end mass 460 and extending though the handpiece housing 456 or a weight applied to the resonator end mass 460; however, alternate stress elements are possible as appreciated by one of ordinary skill in the art.

FIG. 12 is the embodiment of FIG. 8 with the addition of a resonator end mass 460, a sensing coil 462, and a plurality of opening 481, 482 into the end effector for fluid communication between the fluid path 458 and a channel 480 within the end effector 430. In this embodiment, the sensing coil 462 is positioned within the handpiece housing 456 as described for FIG. 11. Handpiece housing 456 partially surrounds the resonator end mass 460 with an inner cup 486 that defines part of the fluid path with the outer wall 488 of the handpiece housing 456 such that the fluid path is between the inner cup 486 and the outer wall 488. The inner cup 486 may be positioned such that the fluid path contacts only a portion of the resonator end mass 460.

Figure 13:
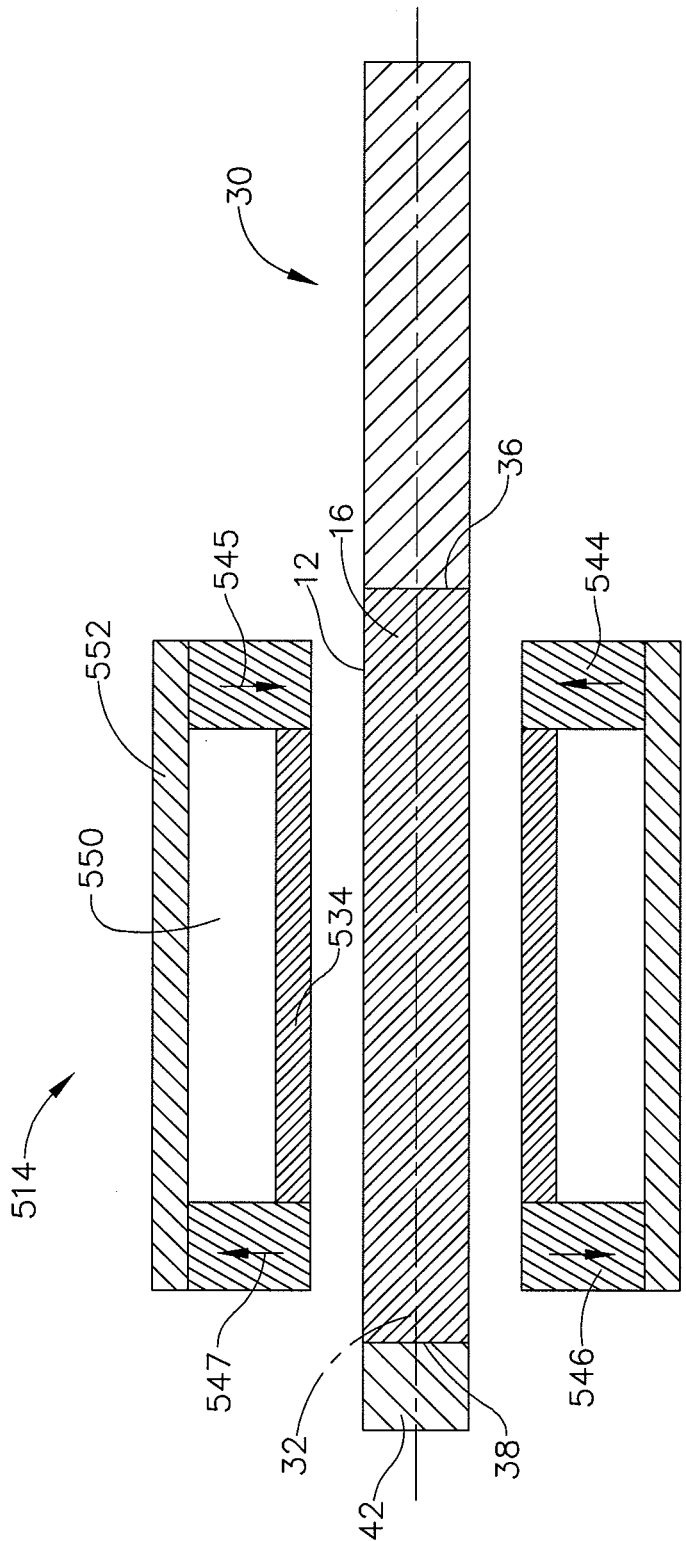
FIGS. 13-14 are views, as in FIG. 1, but of additional embodiments of the medical ultrasound transducer assembly and attached end effector.
Figure 14:
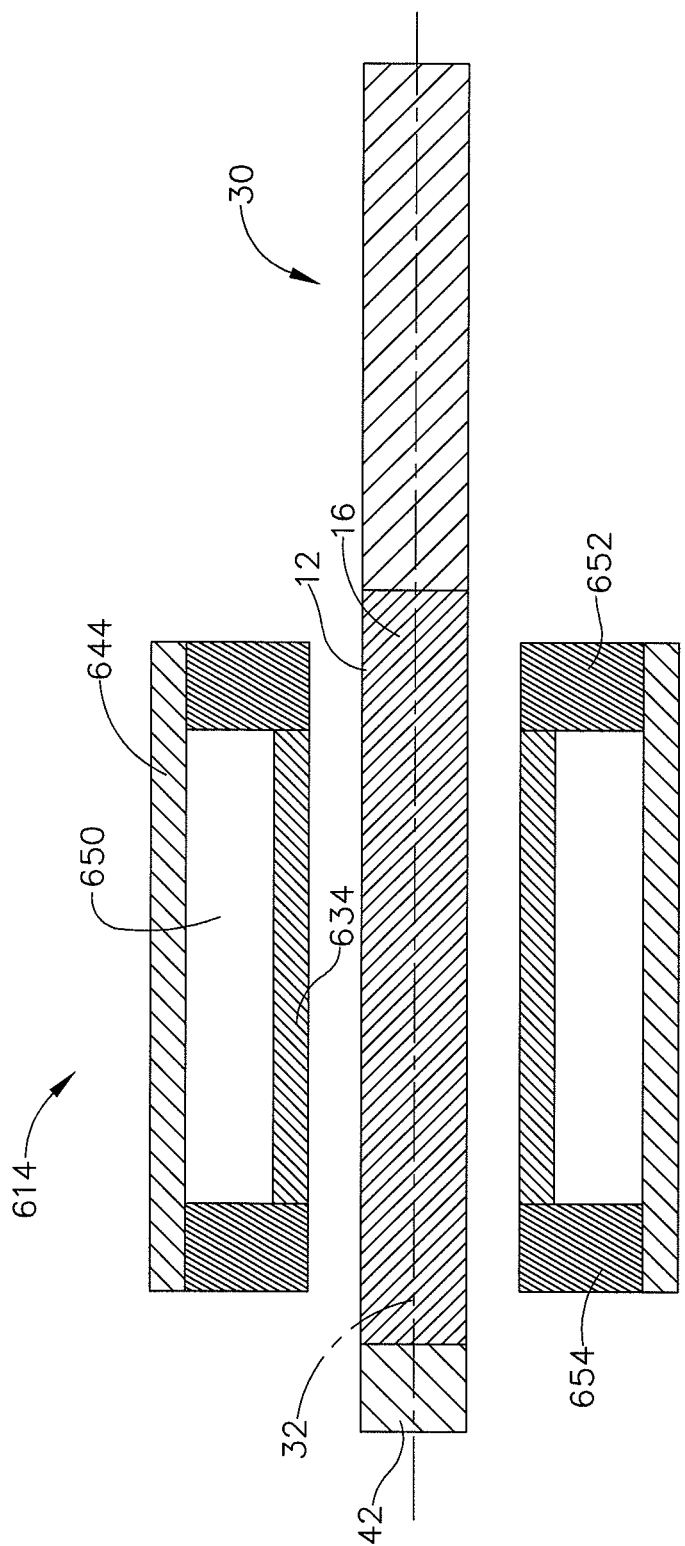

FIGS. 13-14 are views, as in FIG. 1, but of additional embodiments of the medical ultrasound transducer assembly and attached end effector. In one example of an alternative expression of the embodiment of FIG. 1, as shown in FIG. 13, the transducer assembly 514 includes a central longitudinal axis 32, includes an elongated magnetostrictive actuator 12 substantially coaxially aligned with the longitudinal axis 32 and comprising a magnetostrictive alloy 16, and includes a first coil 534 substantially coaxially aligned with the longitudinal axis 32, surrounding the actuator 12, and adapted to excite the actuator 12 to substantially a desired medical resonant frequency and substantially a desired medical amplitude. The actuator 12 has first and second ends 36 and 38, wherein the transducer assembly 514 includes an end effector 30 attached to the first end 36 and a second end mass 42 attached to the second end 38. The magnetostrictive alloy 16 is chosen from the group previously described in the first expression of the first embodiment of the invention.

The transducer assembly 514 includes a second coil 550 substantially coaxially aligned with the longitudinal axis 32, surrounding the first coil 534, and adapted to adjust the bias magnetic field. The transducer assembly 514 includes a first radial permanent magnet 544 and a second radial permanent magnet 546 each substantially coaxially aligned with the longitudinal axis 32 and together longitudinally bounding the first coil 534 and the second coil 550. The first radial permanent magnet 544 has a magnetic field of a first direction 545 and the second radial permanent magnet 546 has a magnetic field of a second direction 547 that is opposite the first direction 545. The first direction 545, as shown in FIG. 13, is radially inward toward the magnetostrictive actuator 12 and the second direction 547 is radially outward away from the magnetostrictive actuator 12.

The transducer assembly 514 also includes a magnetic field collector 552 substantially coaxially aligned with the longitudinal axis 32 and surrounding the first coil 534, the second coil 550, the first radial permanent magnet 544 and the second radial permanent magnet 546.

In another alternative expression of the embodiment of FIG. 1, as shown in FIG. 14, the transducer assembly 614 includes a central longitudinal axis 32, includes an elongated magnetostrictive actuator 12 substantially coaxially aligned with the longitudinal axis 32 and comprising a magnetostrictive alloy 16, and includes a first coil 634 substantially coaxially aligned with the longitudinal axis 32, surrounding the actuator 12, and adapted to excite the actuator 12 to substantially a desired medical resonant frequency and substantially a desired medical amplitude. The actuator 12 has first and second ends 36 and 38, wherein the transducer assembly 614 includes an end effector 30 attached to the first end 36 and a second end mass 42 attached to the second end 38. The magnetostrictive alloy 16 is chosen from the group previously described in the first expression of the first embodiment of the invention.

The transducer assembly 614 includes a second coil 650 substantially coaxially aligned with the longitudinal axis 32, surrounding the first coil 634, and adapted to adjust the bias magnetic field. The transducer assembly 614 includes a first magnetic field collector 652 and a second magnetic field collector 654 each substantially coaxially aligned with the longitudinal axis 32 and together longitudinally bounding the first coil 634 and the second coil 650. The transducer assembly 614 also includes a permanent magnet 644 substantially coaxially aligned with the longitudinal axis 32 and surrounding the first coil 634, the second coil 650, the first magnetic field collector 652, and the second magnetic field collector 654. The permanent magnet 644 may be laminated to the outer surface of the second coil 650 and the first and second magnetic field collectors 652, 654.

Figure 15:
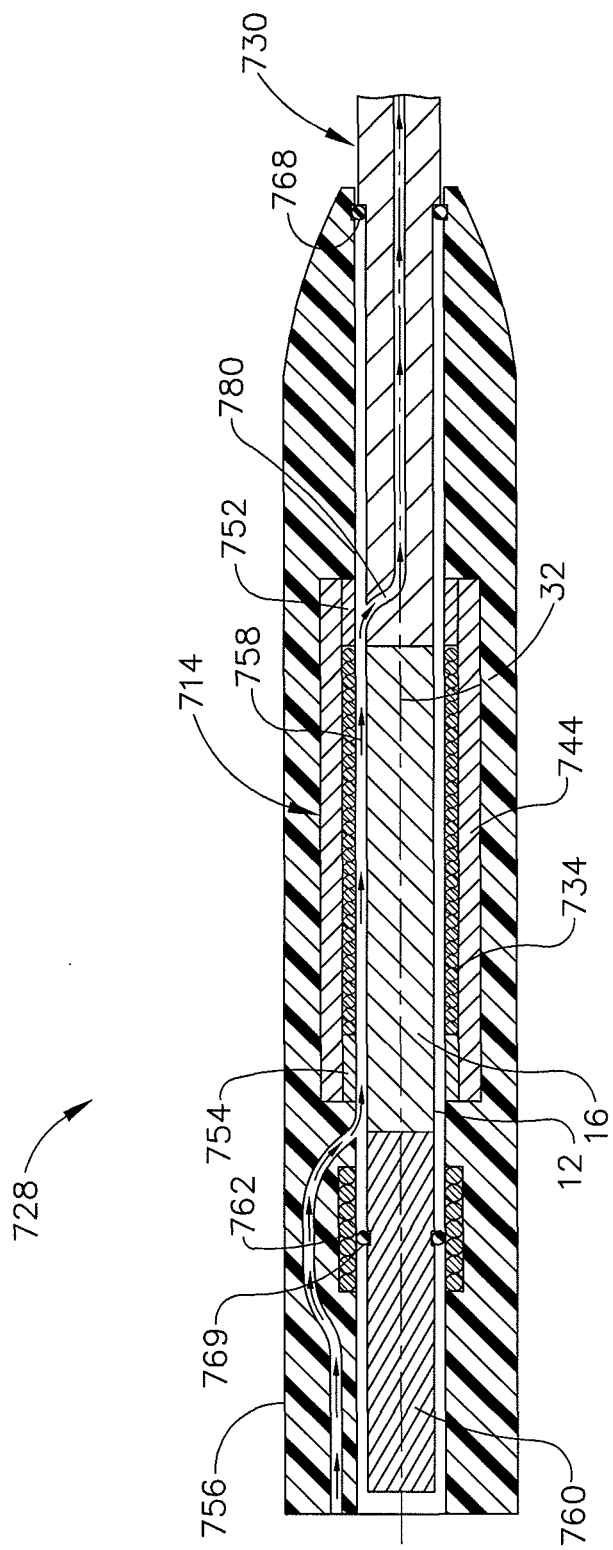
FIGS. 15-16 are views, as in FIG. 5, but of additional embodiments of the handpiece and attached end effector.
Figure 16:
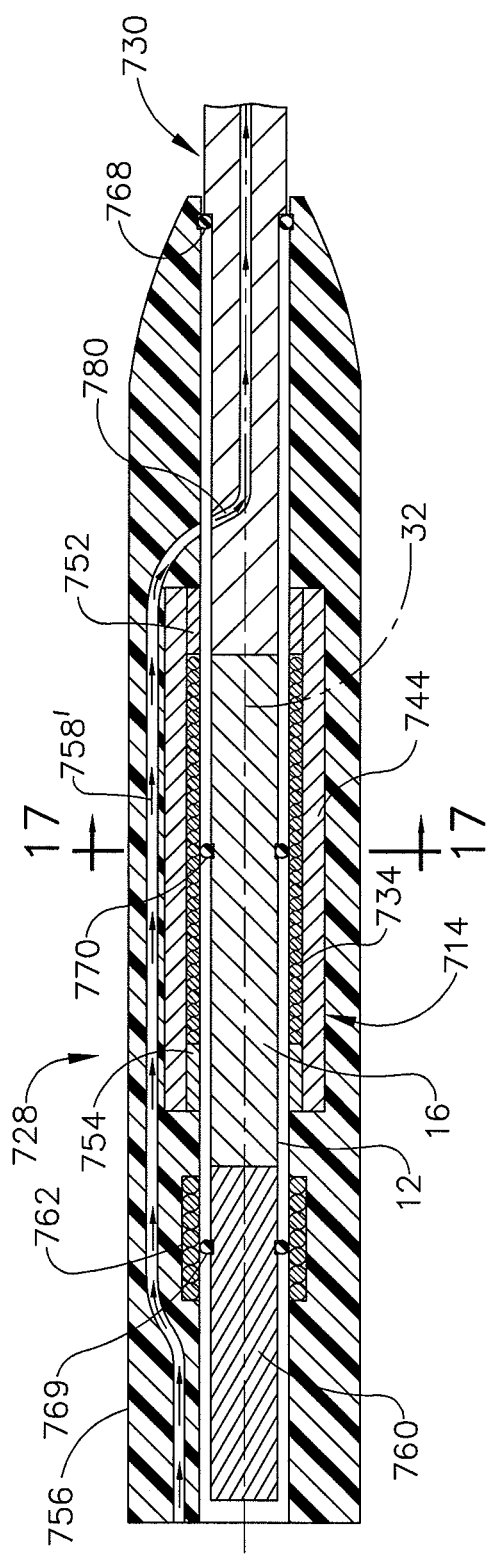

FIGS. 15-16 are views, as in FIG. 5, but of additional embodiments of the handpiece and attached end effector. FIG. 15 is an additional embodiment of a medical ultrasound handpiece 728 including a medical ultrasound transducer assembly 714 adapted to attachingly receive an ultrasonically-driven medical end effector 730. The transducer assembly 714 includes a central longitudinal axis 32, includes an elongated magnetostrictive actuator 12 substantially coaxially aligned with the longitudinal axis 32 and comprising a magnetostrictive alloy 16, includes a first coil 734 substantially coaxially aligned with the longitudinal axis 32, surrounding the actuator 12, and adapted to excite the actuator 12 to substantially a desired medical resonant frequency and substantially a desired medical amplitude, includes a first magnetic field collector 752 and a second magnetic field collector 754 each substantially coaxially aligned with the longitudinal axis 32 and together longitudinally bounding the first coil 734, and includes a permanent magnet 744 substantially coaxially aligned with the longitudinal axis 32, surrounding the first coil 734 and both the first and second magnetic field collectors 752, 754. The magnetostrictive alloy 16 is chosen from the group previously described in the first expression of the first embodiment of the invention. The first coil 734 is transversely spaced apart from the actuator 12. The transducer assembly 714 may also include a resonator end mass 760 and a sensing coil 762.

The handpiece 728 includes a handpiece housing 756 substantially coaxially aligned with the longitudinal axis 32 and surrounds the medical ultrasound transducer assembly 714 and includes a fluid path 758 having a portion thereof disposed between the actuator 12 and the first coil 734 and connects to a fluid channel 780 in the end effector 730 when the end effector is attachingly received by the transducer assembly.

FIG. 16 is an alternate embodiment of FIG. 15 that differs in the placement of the fluid path and has an additional O-ring. Fluid path 758' of FIG. 16 is disposed within the handpiece housing with a portion thereof between the outer surface of the handpiece housing and the medical ultrasound transducer assembly 714. Fluid path 758' connects to a fluid channel 780 in the end effector 730 when the end effector is attachingly received by the transducer assembly.

Figure 17:
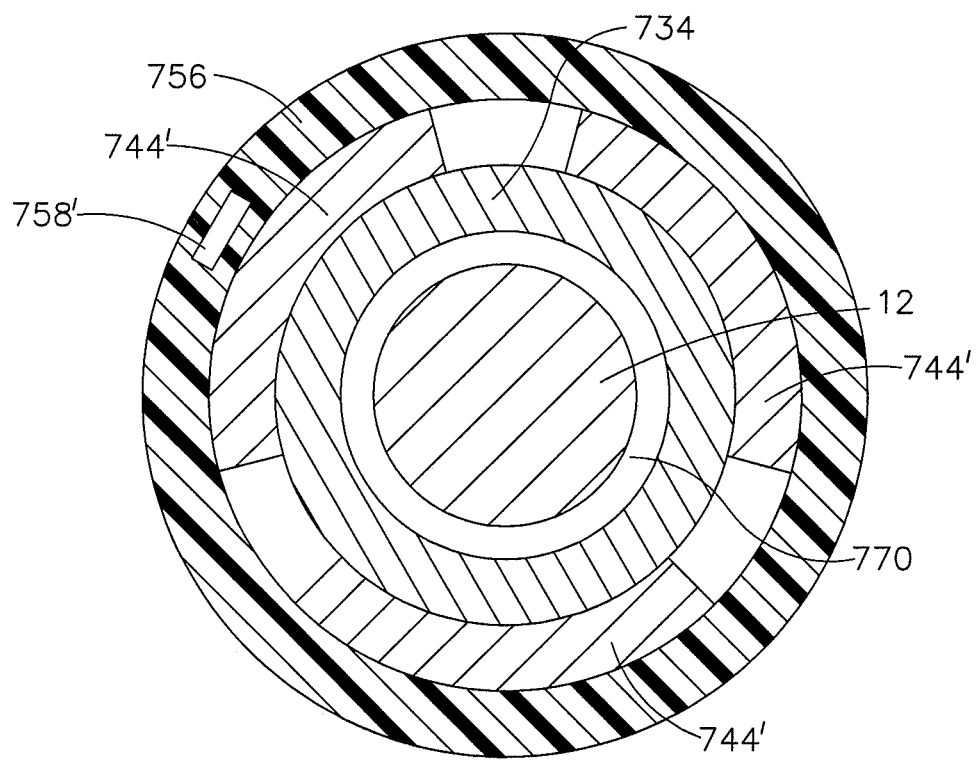
FIG. 17 is a cross-sectional view of the handpiece of FIG. 16, taken along lines 17-17 of FIG. 16, showing that the ferrite/permanent magnet of FIG. 16 is an array of circumferentially-spaced apart magnet segments creating a fluid path between the segments.

It is noted that permanent magnet 744 in FIGS. 15 and 16 may also be a ferrite magnet. Permanent magnet 744 is a completely annular magnet in FIG. 15 and is an array of circumferentially-spaced-apart magnet segments 744' in FIG. 16 (as shown in the cross-sectional view in FIG. 17).

It is noted, from FIGS. 15-16 that magnetic biasing with low eddy current losses, for any of the previously described and/or illustrated embodiments, can be provided with a ferrite magnet as well as with a permanent magnet (note the component labeled "ferrite/permanent magnet" in FIGS. 15-16). In one example of any one or more or all of the previously described and/or illustrated embodiments, the magnetic biasing circuit is a closed magnetic biasing circuit, and/or the end effector is a pair of shears having its harmonic blade attachingly received by the medical ultrasound transducer assembly, and/or blade impedance and necessary phase margin are taken into account to drive the end effector, and/or the primary excitation mode of the actuator and the end effector is longitudinal.

Several benefits and advantages are obtained from one or more of the expressions of embodiments of the invention. In one example, the magnetostrictive actuator consists essentially of a magnetostrictive alloy chosen from the previously-described group and optionally includes dopants. In this example, the magnetostricitve alloy should provide a ductile magnetostrictive actuator (unlike the brittle Terfenol-D alloy of the known dental scaler which would need to be compressed for durability). In this example, the higher-magnetic-saturation limit of the chosen magnetostrictive alloy should be able to be housed in a small-diameter, ergonomic handpiece housing and drive a larger-diameter medical end effector (compared to the smaller-diameter end effector of the known dental scaler having the nickel actuator, such smaller diameter providing a necessary acoustic gain because of the lower magnetic saturation limit of nickel). It is noted that dental scalers are low power devices used to remove scale from teeth and are not powerful enough to efficiently sculpt teeth or remove bone, whereas examples of the embodiments of the invention should be able to sculpt teeth and cut bone.

While the present invention has been illustrated by a description of several expressions, embodiments, and examples, etc. thereof, it is not the intention of the applicant to restrict or limit the spirit and scope of the appended claims to such detail. Numerous other variations, changes, and substitutions will occur to those skilled in the art without departing from the scope of the invention. It will be understood that the foregoing description is provided by way of example, and that other modifications may occur to those skilled in the art without departing from the scope and spirit of the appended Claims.

What is claimed is:

1. Apparatus comprising:
a magnetostrictive actuator of a medical ultrasound transducer assembly that has an end effector and a central longitudinal axis through the end effector, the magnetostrictive actuator having a first end and a second end, and further comprising an end mass, that has magnetostrictive properties or is a soft magnetic collector, acoustically connected to at least one of the first and second ends of the magnetostrictive actuator; wherein the magnetostrictive actuator comprises:
an elongated magnetostrictive alloy substantially coaxially alignable with the longitudinal axis of the medical ultrasound transducer assembly,
wherein the magnetostrictive alloy is coupleable to the end effector to provide the end effector with a longitudinal, standing wave vibration amplitude at its distal antinode tip equal to substantially the vibrational amplitude of the magnetostrictive actuator.

2. The apparatus of claim 1, wherein the actuator includes a plurality of lamination layers each comprising the magnetostrictive alloy.

3. The apparatus of claim 2, wherein the magnetostrictive alloy of each lamination layer is electrically insulated from the magnetostrictive alloy of each neighboring lamination layer.

4. The apparatus of claim 1, wherein the actuator comprises a composite material, wherein the composite material includes a magnetostrictively-inactive matrix and the magnetostrictive alloy, and wherein the magnetostrictive alloy is distributed in the matrix.

5. The apparatus of claim 4, wherein the magnetostrictive alloy has a first electrical conductivity, and wherein the matrix has a second electrical conductivity which is lower than the first electrical conductivity.

6. A medical ultrasound handpiece comprising a medical ultrasound transducer assembly adapted to attachingly receive an ultrasonically-driven medical end effector, wherein the transducer assembly includes:
a central longitudinal axis,
an elongated magnetostrictive actuator substantially coaxially aligned with the longitudinal axis and comprising a magnetostrictive alloy,
a first coil substantially coaxially aligned with the longitudinal axis, surrounding the actuator, and adapted to excite the actuator to substantially a desired medical resonant frequency and substantially a desired medical amplitude, and
wherein the transducer assembly includes one or more permanent magnets substantially coaxially aligned with the longitudinal axis, surrounding at least the actuator, and adapted to create a bias magnetic field for a desired operating point on a strain versus magnetic field graph of the magnetostrictive alloy;
wherein the magnetostrictive alloy is chosen from the group consisting of an alloy comprising iron and gallium, an alloy comprising iron and aluminum, an alloy comprising iron, gallium and aluminum, an alloy comprising cobalt, manganese and gallium, an alloy comprising nickel, manganese and gallium, an alloy comprising cobalt, manganese and aluminum, an alloy comprising nickel, manganese and aluminum, an alloy comprising cobalt, nickel, manganese and gallium, an alloy comprising cobalt, nickel, manganese and aluminum, an alloy comprising cobalt, manganese, gallium and aluminum, an alloy comprising nickel, manganese, gallium, and aluminum, and an alloy comprising cobalt, nickel, manganese, aluminum and gallium.

7. The medical ultrasound handpiece of claim 6, wherein the actuator has first and second ends, wherein the transducer assembly includes a first end mass attached to the first end of the actuator and a second end mass attached to the second end of the actuator, and wherein the first end mass is adapted to attachingly receive the end effector.

8. The medical ultrasound handpiece of claim 6, wherein the transducer assembly includes a second coil substantially coaxially aligned with the longitudinal axis, surrounding at least the first coil, and adapted to adjust the bias magnetic field.

9. The medical ultrasound handpiece of claim 8, wherein the transducer assembly includes a first permanent magnet and a second permanent magnet that together longitudinally bound the first coil and the second coil.

10. The medical ultrasound handpiece of claim 8, wherein the transducer assembly includes one or more magnetic field collectors each substantially coaxially aligned with the longitudinal axis.

11. The medical ultrasound handpiece of claim 10, wherein the transducer assembly includes a first magnetic field collector and a second magnetic field collector, wherein the first and second magnetic field collectors together longitudinally bound at least the first coil.

12. The medical ultrasound handpiece of claim 6, wherein the first coil is transversely spaced apart from the actuator, and also including a handpiece housing and a fluid path, wherein the handpiece housing is substantially coaxially aligned with the longitudinal axis and surrounds the first coil.

13. The medical ultrasound handpiece of claim 12, wherein the fluid path includes a portion disposed between the actuator and the first coil.

14. The medical ultrasound handpiece of claim 12, wherein the fluid path is within the handpiece housing and includes a portion disposed between the outer surface of the handpiece housing and the transducer assembly.

15. The medical ultrasound handpiece of claim 12, wherein the fluid path is at least one of an irrigation and a suction path and is in fluid communication with the end effector when the end effector is attachingly received by the transducer assembly.

16. The medical ultrasound handpiece of claim 12, wherein the fluid path is a recirculation coolant path and is in fluid communication with the end effector when the end effector is attachingly received by the transducer assembly.

17. The medical ultrasound handpiece of claim 6, wherein the transducer assembly includes a resonator end mass and a sensing coil, wherein the resonator end mass is substantially coaxially aligned with the longitudinal axis, is acoustically connected to one end of the magnetostrictive actuator, and has magnetostrictive properties, and wherein the sensing coil is substantially coaxially aligned with the longitudinal axis, surrounds the resonator end mass, and is adapted to provide feedback on actuator vibrational frequency and actuator vibrational amplitude for controlling the actuator to maintain substantially the desired medical resonant frequency and the desired medical amplitude.

18. The medical ultrasound handpiece of claim 6, wherein the actuator is free of mechanical compression.

19. A medical ultrasound system comprising;
   a handpiece housing,
   a first medical ultrasound transducer assembly, and
   an ultrasonically-driven first medical end effector attachable to the first medical ultrasound transducer assembly, wherein the first medical ultrasound transducer assembly includes:
      a first central longitudinal axis; and
      an elongated magnetostrictive first actuator substantially coaxially aligned with the longitudinal axis and comprising a first magnetostrictive alloy, the magnetostrictive actuator having a first end and a second end, and further comprising an end mass, that has magnetostrictive properties or is a soft magnetic collector, acoustically connected to at least one of the first and second ends of the magnetostrictive actuator;
      wherein the magnetostrictive actuator has a first end and a second end, wherein the first end if coupleable to the end effector and the second end is acoustically connected to an end mass that has magnetostrictive properties or is a soft magnetic collector;
   wherein at least a portion of the first medical ultrasound transducer assembly is attachingly insertable in the handpiece housing without the use of tools, without damage to the handpiece housing, and without damage to the first medical ultrasound transducer assembly, and
   wherein the first magnetostrictive alloy is chosen from the group consisting of an alloy comprising iron and gallium, an alloy comprising iron and aluminum, an alloy comprising iron, gallium and aluminum, an alloy comprising cobalt, manganese and gallium, an alloy comprising nickel, manganese and gallium, an alloy comprising cobalt, manganese and aluminum, an alloy comprising nickel, manganese and aluminum, an alloy comprising cobalt, nickel, manganese and gallium, an alloy comprising cobalt, nickel, manganese and aluminum, an alloy comprising cobalt, manganese, gallium and aluminum, an alloy comprising nickel, manganese, gallium, and aluminum, and an alloy comprising cobalt, nickel, manganese, aluminum and gallium.

20. The medical ultrasound system of claim 19, wherein the first medical ultrasound transducer assembly is removable from the handpiece housing without the use of tools, without damage to the handpiece housing, without damage to the first medical ultrasound transducer assembly, and without damage to the first medical end effector.

21. The medical ultrasound system of claim 20, also including a second medical ultrasound transducer assembly and an ultrasonically-driven second medical end effector attachable to the second medical ultrasound transducer assembly, wherein the second medical ultrasound transducer assembly includes a second central longitudinal axis and includes an elongated magnetostrictive second actuator substantially coaxially aligned with the second longitudinal axis and comprising a second magnetostrictive alloy, wherein at least a portion of the second medical ultrasound transducer assembly is attachingly insertable in the handpiece housing and is manually removable from the handpiece housing without the use of tools, without damage to the handpiece housing, without damage to the second medical ultrasound transducer assembly, and without damage to the second medical end effector, wherein the second medical end effector is different from the first medical end effector, and wherein the second magnetostrictive alloy is chosen from the group consisting of an alloy comprising iron and gallium, an alloy comprising iron and aluminum, an alloy comprising iron, gallium and aluminum, an alloy comprising cobalt, manganese and gallium, an alloy comprising nickel, manganese and gallium, an alloy comprising cobalt, manganese and aluminum, an alloy comprising nickel, manganese and aluminum, an alloy comprising cobalt, nickel, manganese and gallium, an alloy comprising cobalt, nickel, manganese and aluminum, an alloy comprising cobalt, manganese, gallium and aluminum, an alloy comprising nickel, manganese, gallium, and aluminum, and an alloy comprising cobalt, nickel, manganese, aluminum and gallium.

22. The medical ultrasound system of claim 21, wherein the second medical end effector is attachable to and removable from the second medical ultrasound transducer assembly without damage to the second medical end effector and without damage to the second medical ultrasound transducer assembly, and wherein the first medical end effector is attachable to and removable from the first medical ultrasound transducer assembly without damage to the first medical end effector and without damage to the first medical ultrasound transducer assembly.

23. The apparatus of claim 1 wherein the magnetostrictive alloy is chosen from the group consisting of an alloy comprising iron and gallium, an alloy comprising iron and aluminum, an alloy comprising iron, gallium and aluminum, an alloy comprising cobalt, manganese and gallium, an alloy comprising nickel, manganese and gallium, an alloy comprising cobalt, manganese and aluminum, an alloy comprising nickel, manganese and aluminum, an alloy comprising cobalt, nickel, manganese and gallium, an alloy comprising cobalt, nickel, manganese and aluminum, an alloy comprising cobalt, manganese, gallium and aluminum, an alloy comprising nickel, manganese, gallium, and aluminum, and an alloy comprising cobalt, nickel, manganese, aluminum and gallium.

24. The apparatus of claim 1 further comprising an end mass directly coupled to the magnetostrictive alloy and coupleable to the end effector such that the magnetostrictive alloy is indirectly coupleable to the end effector.

25. The apparatus of claim 6, wherein the magnetostrictive actuator has a first end and a second end, wherein the first end is coupleable to the end effector and the second end is acoustically connected to an end mass that has magnetostrictive properties or is a soft magnetic collector.

26. The apparatus of claim 1, further comprising a sensing coil substantially coaxially aligned with the longitudinal axis, surrounding the end mass, and adapted to provide feedback on actuator vibrational frequency and actuator vibrational amplitude for controlling the actuator to maintain substantially the desired medical resonant frequency and the desired medical amplitude.

* * * * *